United States Patent
Smith et al.

(10) Patent No.: US 10,247,703 B2
(45) Date of Patent: Apr. 2, 2019

(54) INSPECTION DEVICE UTILIZING EDDY CURRENTS

(71) Applicant: United Technologies Corporation, Farmington, CT (US)

(72) Inventors: Kevin D. Smith, Glastonbury, CT (US); Jonathan P. Sullivan, Manchester, CT (US); David A. Raulerson, Palm Beach Garden, FL (US)

(73) Assignee: United Technologies Corporation, Farmington, CT (US)

( * ) Notice: Subject to any disclaimer, the term of this patent is extended or adjusted under 35 U.S.C. 154(b) by 168 days.

(21) Appl. No.: 15/375,557

(22) Filed: Dec. 12, 2016

(65) Prior Publication Data

US 2017/0122910 A1 May 4, 2017

Related U.S. Application Data

(62) Division of application No. 12/713,410, filed on Feb. 26, 2010, now Pat. No. 9,551,689.

(51) Int. Cl.
*G01N 27/90* (2006.01)
*G01B 7/14* (2006.01)
*G01M 15/14* (2006.01)

(52) U.S. Cl.
CPC ............ *G01N 27/9053* (2013.01); *G01B 7/14* (2013.01); *G01M 15/14* (2013.01)

(58) Field of Classification Search
CPC ...... G01N 27/66; G01N 27/90; G01N 27/904; G01N 27/9053
See application file for complete search history.

(56) References Cited

U.S. PATENT DOCUMENTS

| | | |
|---|---|---|
| 3,898,562 A | 8/1975 | Mizikar |
| 4,139,822 A | 2/1979 | Urich et al. |
| 4,584,549 A | 6/1986 | Smith et al. |
| 4,659,988 A | 4/1987 | Goff et al. |
| 4,668,912 A | 5/1987 | Junker |
| 4,719,422 A | 1/1988 | deWalle et al. |

(Continued)

FOREIGN PATENT DOCUMENTS

| | | |
|---|---|---|
| EP | 1621878 | 2/2006 |
| EP | 2040069 | 3/2009 |
| WO | 2009004319 | 1/2009 |

OTHER PUBLICATIONS

European Search Report for Application No. 11156026.4 dated May 20, 2011.

*Primary Examiner* — Eisa B Elhilo
(74) *Attorney, Agent, or Firm* — Carlson, Gaskey & Olds, P.C.

(57) ABSTRACT

An exemplary method of inspecting a component includes, among other things, securing an inspection probe body relative to a component, using a sensor assembly housed within the inspection probe body to induce an eddy current in a target area of the component, the target area having a target surface that is spaced from the sensor assembly, sensing a parameter of the eddy current in the component using the sensor assembly, and determining a position of the target surface of the component relative to the inspection probe body using the parameter of eddy current from the sensing.

15 Claims, 2 Drawing Sheets

(56) References Cited

U.S. PATENT DOCUMENTS

| | | | |
|---|---|---|---|
| 5,019,777 A | * | 5/1991 | Gulliver ............... B82Y 15/00 |
| | | | 324/202 |
| 5,130,651 A | | 7/1992 | Morrey, Jr. |
| 5,140,264 A | | 8/1992 | Metala et al. |
| 5,442,286 A | | 8/1995 | Sutton, Jr. et al. |
| 5,576,492 A | | 11/1996 | Phalin |
| 5,903,147 A | | 5/1999 | Granger, Jr. et al. |
| 6,040,695 A | | 3/2000 | Raulerson et al. |
| 6,545,467 B1 | | 4/2003 | Batzinger et al. |
| 6,949,922 B2 | | 9/2005 | Twerdochlib et al. |
| 6,952,094 B1 | | 10/2005 | Viertl |
| 2003/0222638 A1 | | 12/2003 | Twerdochlib |
| 2009/0178417 A1 | | 7/2009 | Draper et al. |

* cited by examiner

INSPECTION DEVICE UTILIZING EDDY CURRENTS

CROSS-REFERENCE TO RELATED APPLICATION

This application is a divisional of U.S. application Ser. No. 12/713,410 filed on Feb. 26, 2010.

BACKGROUND

This invention relates generally to an inspection device. More particularly, this invention relates to an inspection probe that utilizes eddy currents.

Turbo machinery, such as gas turbine engines are known and include multiple sections, such as a fan section, a compression section, a combustor section, and a turbine section. During stable operation, the fan section moves air into the machinery. The air is compressed as the air flows through the compression section. The compressed air is then mixed with fuel and combusted in the combustor section. Products of the combustion are expanded in the turbine section to rotatably drive the machinery.

The performance of the machinery depends, in part, on relationships and interfaces between components of the machinery. Accordingly, components of the machinery are periodically inspected to determine their dimensions, clearances, spacing, and other information. The information obtained during the inspection can highlight potential relationship and interface issues.

For example, the size of components can change as the components wear during machinery operation, machinery cleaning, machinery maintenance, etc. Worn components can result in inefficiencies. In one specific example, disks in the turbine section of an engine include slots for holding turbine blades. The slots have a relatively complex geometry and are sometimes difficult to measure due to their axial depth. The dimensions of the slots change when the disk erodes during cleaning. The slots in the eroded disk may fail to securely hold the turbine blades.

SUMMARY

A method of inspecting a component according to an exemplary non-limiting aspect of the present disclosure includes, among other things, securing an inspection probe body relative to a component, using a sensor assembly housed within the inspection probe body to induce an eddy current in a target area of the component. The target area has a target surface that is spaced from the sensor assembly. The method further includes sensing a parameter of the eddy current in the component using the sensor assembly, and determining a position of the target surface of the component relative to the inspection probe body using the parameter of eddy current sensed from the sensing.

In another example of the foregoing method, a voltage of the eddy current sensed is the parameter of the eddy current used in the determining.

In another example of any of the foregoing methods, the determining comprises determining a position of the first surface of the component relative to a reference surface of the component.

Another example of any of the foregoing methods includes using a second sensor assembly housed within the inspection probe body to induce an eddy current in a second area of the component. The second area has a second surface and the second sensor assembly spaced from the second surface. The method includes determining spacing between the first surface, the reference surface, the second surface, or some combination of these.

In another example of any of the foregoing methods, the first surface and the reference surface establish portions of a blade slot in a turbine engine disk.

In another example of any of the foregoing methods, the first surface is transverse the reference surface.

Another example of any of the foregoing methods includes actuating portions of the inspection probe body to secure the inspection probe body relative to the component.

In another example of any of the foregoing methods, the component is a disk in a turbine engine.

In another example of any of the foregoing methods, the target surface establishes a portion of an axially extending slot within the disk.

Another example of any of the foregoing methods includes moving the inspection probe body into contact with the component during the securing using an actuator.

In another example of any of the foregoing methods, the sensor assembly is entirely spaced from the target surface.

Another example of any of the foregoing methods includes contacting a portion of the component with the inspection probe body during the securing.

Another example of any of the foregoing methods includes contacting the portion of the component with the inspection probe body at a position that is directly adjacent the sensor assembly.

In another example of any of the foregoing methods, the inspection probe body contacts the portion of the component at one or more reference surfaces and further comprising calculating at least one distance between the one or more reference surfaces and the target surface.

In another example of any of the foregoing methods, the sensor assembly is a first sensor assembly and the target surface is a first target surface. At least one second sensor assembly is housed within the inspection probe body. The at least one second sensor assembly is associated with at least one respective second target surface of the component. The method includes calculating the position of the at least one second target surface relative to the first target surface.

A method of inspecting a component according to another exemplary non-limiting aspect of the present disclosure includes, among other things, moving an inspection probe body into contact with a portion of turbine machinery component, using a sensor assembly housed within the inspection probe body to induce an eddy current in a target area of the turbine machinery component. The target area having a target surface that is spaced from the sensor assembly. The method includes sensing a parameter of the eddy current in the turbine machinery component using the sensor assembly, and determining a position of the target surface of the component relative to the inspection probe using the parameter of eddy current sensed in the sensing.

These and other features of the example disclosure can be best understood from the following specification and drawings, the following of which is a brief description:

DETAILED DESCRIPTION

Figure 1:
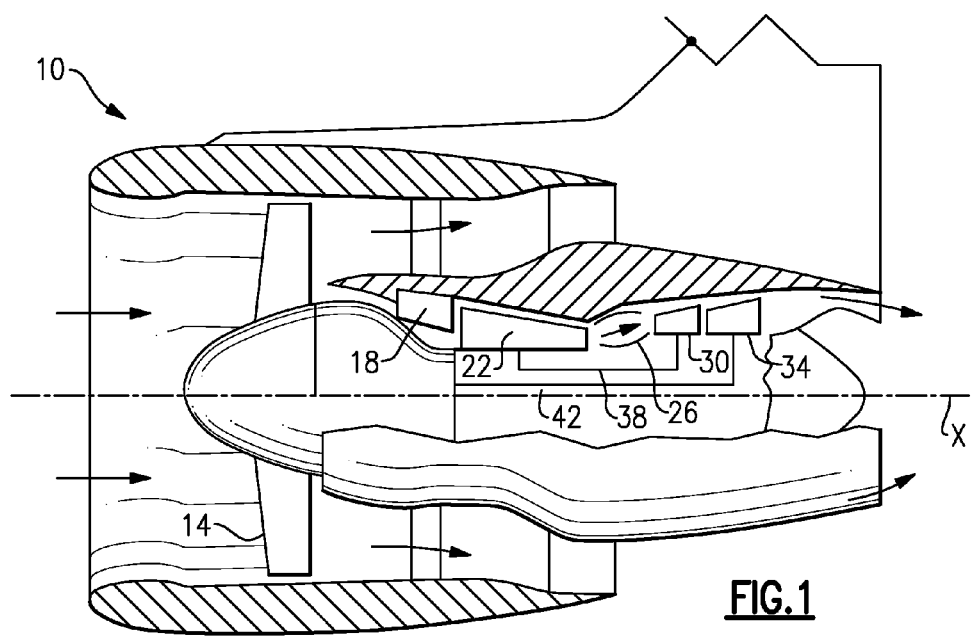
FIG. 1 shows a cross-section of an example gas turbine engine.
Figure 2:
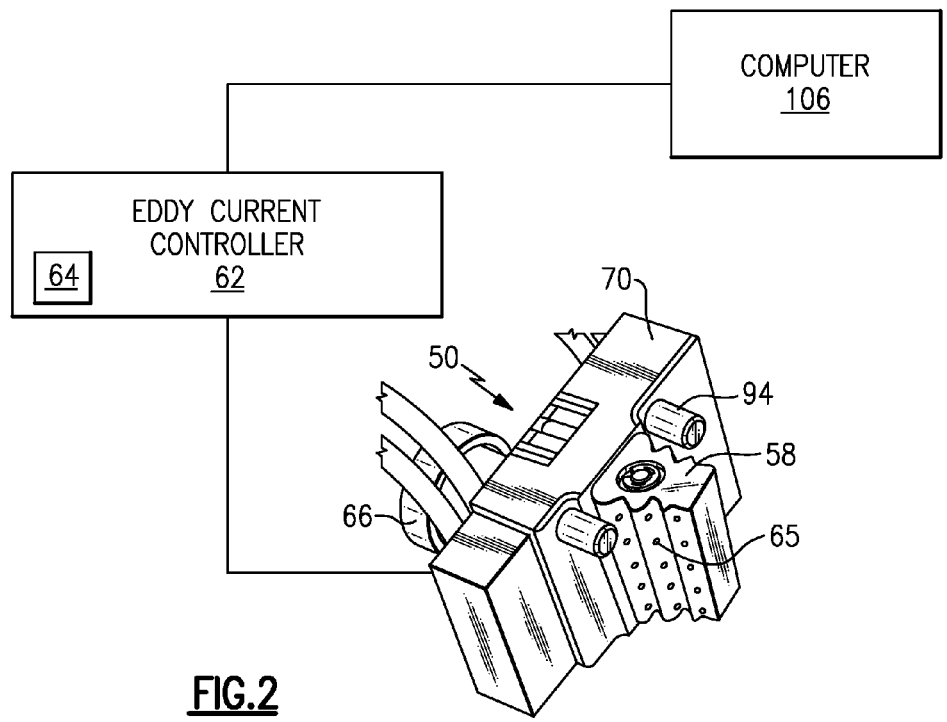
FIG. 2 shows a perspective view of an example inspection probe.
Figure 3:
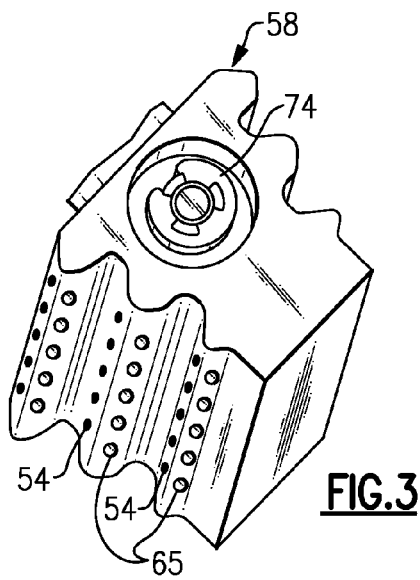
FIG. 3 shows a perspective view of a probe body in the FIG. 2 inspection probe.
Figure 6:
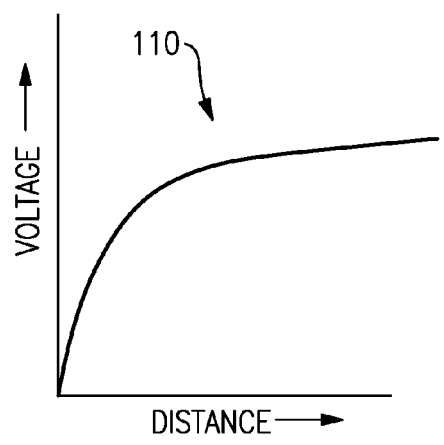
FIG. 6 shows an example lift-off curve used to determine a position of a component in the FIG. 1 engine.

FIG. 1 schematically illustrates an example gas turbine engine 10, which is an example type of turbine machinery. The example gas turbine engine 10 includes (in serial flow communication) a fan section 14, a low-pressure compressor 18, a high-pressure compressor 22, a combustor 26, a high-pressure turbine 30, and a low-pressure turbine 34. The gas turbine engine 10 is circumferentially disposed about an engine centerline X.

During operation, air is pulled into the gas turbine engine 10 by the fan section 14. Some of the air moves to a core of the gas turbine engine 10 and is pressurized by the compressors 18 and 22, mixed with fuel, and burned in the combustor 26. The turbines 30 and 34 extract energy from the hot combustion gases flowing from the combustor 26.

In a two-spool design, the high-pressure turbine 30 utilizes the extracted energy from the hot combustion gases to power the high-pressure compressor 22 through a high speed shaft 38, and the low-pressure turbine 34 utilizes the extracted energy from the hot combustion gases to power the low-pressure compressor 18 and the fan section 14 through a low speed shaft 42.

The examples described in this disclosure are not limited to the two-spool engine architecture described, however, and may be used in other architectures, such as a single-spool axial design, a three-spool axial design, and still other architectures. Further, although the examples discussed herein are described with regard to the gas turbine engine 10, those having skill in this art and the benefit of this disclosure will understand that other examples may include other types of turbine machinery or any component comprising at least some conductive material.

Referring to FIGS. 2-5 with continuing reference to FIG. 1, an example inspection probe assembly 50 includes a multiple of eddy current sensors 54 housed in a probe body 58. The eddy current sensors 54 form a portion of an eddy current sensor assembly. The eddy current sensors 54 are linked to a controller 62 and an eddy current generator 64, which also form a portion of the example eddy current sensor assembly. Access holes 65 in the probe body 58 facilitate securing the sensor tips 54 relative to the probe body 58.

In this example, a pneumatic cylinder 66 is mounted to a housing 70 and the probe body 58. The cylinder 66 is configured to move the probe body 58 and the eddy current sensors 54 relative to the housing 70. A pin arrangement 74 secures the probe body 58 to a shaft of the cylinder 66.

The example inspection probe assembly 50 is used to determine dimensions of a turbine blade slot 78 established within a turbine disk 82 of the gas turbine engine 10. The turbine disk 82 and the turbine blade slot 78 are components of the high-pressure turbine 30 in this example. The turbine blade slot 78 is configured to slidably receive a turbine blade.

As known, processes used to clean the disk, such as grit blasting processes, can alter the profile of the turbine blade slot 78. The example inspection probe assembly 50 can identify altered areas of the turbine blade slot 78.

The probe body 58 includes a plurality of teeth 86a-86c configured to be received within a corresponding area 90a-90c of the disk 82. The example probe body 58 is configured to have a profile that is similar to the profile of the slot 78.

Figure 4:
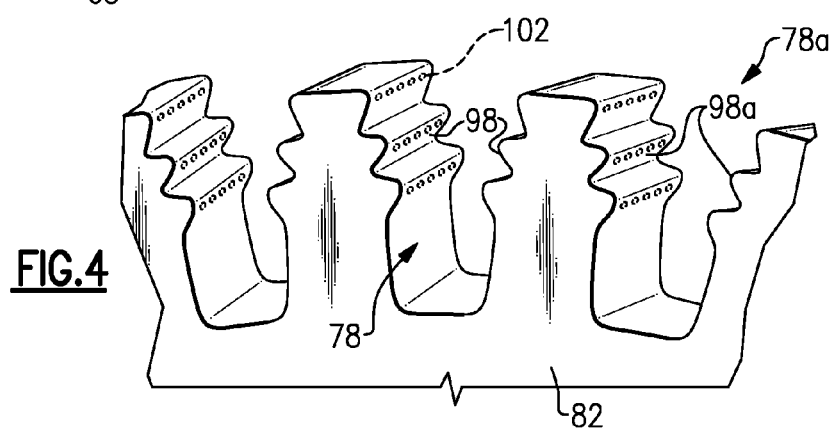
FIG. 4 shows a perspective view of an example disk of the FIG. 1 engine having a blade slot.
Figure 5:
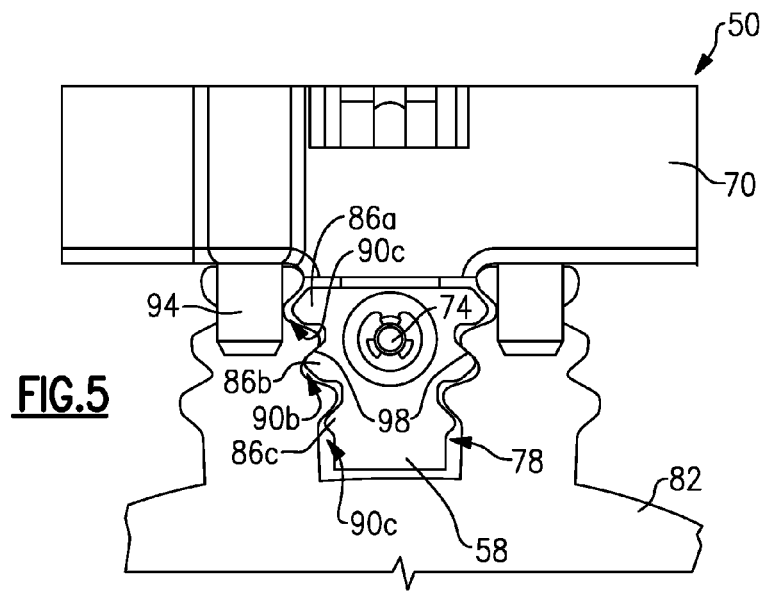
FIG. 5 shows a partial schematic side view of the FIG. 2 inspection probe in an installed position within the FIG. 3 blade slot.

In this example, the probe body 58 is sized such that the teeth 86b contact the disk 82, and the teeth 86a and 86c are spaced from the disk 82 when the inspection probe assembly 50 is in the installed position shown in FIG. 4. The installed position is a position appropriate for determining spacing of the slot 78.

To move the inspection probe assembly 50 to the installed position, the probe body 58 is first slid axially into the slot 78. Cylindrical stops 94 limit the axial sliding movement in this example.

The cylinder 66 is then activated, which pulls the probe body 58 radially outward relative to the housing 70. Contact between the teeth 86b and the disk 82 limits further radial movement of the probe body 58. In another example, the probe body 58 is moved manually rather than using the cylinder 66.

In this example, a surface of the probe body 58 contacts the disk 82 at the teeth 86b. The probe body 58 is made from a glass reinforced plastic material. Other suitable materials include other materials that are not likely to scratch or otherwise mar the surfaces of the disk 82.

Notably, the eddy current sensors 54 in the area of the teeth 86b contacting the disk 82 are positioned below the surface of the probe body 58 such that the eddy current sensors 54 in this area are spaced from the disk 82.

The eddy current sensors 54 in other areas of the probe body 58 are also positioned below the surface of the probe body 58. In another example, these eddy current sensors 54 are flush with the surface of the probe body 58. As can be appreciated, eddy current sensors 54 flush with the surface of the probe body 58 in the other areas would still be spaced from the disk 82 as these other areas of the probe body 58 are spaced from the disk 82.

In this example, the teeth 86b contact the disk 82 at reference surfaces 98. Dimensions and other measurements associated with the slot 78 are established, in part, using the location of the reference surfaces 98.

The eddy current sensors 54 are distributed throughout the probe body 58. Each of the eddy current sensors 54 is configured to induce an eddy current in an associated area of the disk 82. Each of those areas have a target surface 102 that establishes a portion of the slot 78. In this example, the target surface 102 corresponds to the area of the disk 82 closest to the respective eddy current sensor tip 54. The eddy current sensors 54 are positioned in various radial and axial positions within the probe body 58. Target surfaces 102 are thus also distributed in this manner.

After inducing the eddy current, the eddy current sensors 54 detect a parameter of the eddy current such as the voltage of the eddy current in that area of the disk 82. A computer 106, using the strength of the voltage, then determines a distance between each of the eddy current sensors 54 and the associated target surface 102. The computer 106 acts as a data acquisition and analysis system for the inspection probe assembly 50.

The computer 106 associates one of the eddy current sensors 54 detecting a lower eddy current voltage as being spaced closer to the target area 102 associated with that eddy current sensor tip 54 than another eddy current sensor tip 54 that detects a higher eddy current in another target surface 102. In one example, the computer 106 utilizes a lift-off curve 110 (FIG. 5) when determining more precise spacing.

The computer 106 then establishes dimensions of the slot 78, for example, using the distances between each of the eddy current sensors 54 and their associated target surface 102. The computer 106 also uses the location of the reference surface 98 in one example.

The positioning of the probe body 58 relative to the slot 78 is reproducible in another slot 78a. Thus the computer 106 may output a comparison of spacing in the slot 78 to the slot 78a. Aligning the probe body 58 relative to the reference surfaces 98 in the slot 78, and the aligning the reference surfaces 98a in the slot 78a facilitates reproducing the position of the probe body 58. The cylinder 66 is deactivated so that the probe body 58 can be moved from the installed position within the slot 78 to an installed position within the slot 78a.

The dimensioning of the probe body 58 and the eddy current sensors 54 is known and remains consistent and stable whether the probe body 58 is in the slot 78 or the slot 78a. Thus, differences in voltages detected by the eddy current sensors 54 can typically be attributed to differences in the surfaces of the slots 78 and 78a.

The example computer 106 uses the dimensions to detect dimensional irregularities in the slot 78. In one example, the dimensional information is compared to acceptable dimensions to determine irregularities. The computer 106 may establish a general profile of the slot 78 using the dimensional information.

Features of this invention include a relatively simple inspection tool that is easily transported, installed, and set-up. The invention also provides information about variations in the surface along the axial depth of the inspected component.

Although a preferred embodiment has been disclosed, a worker of ordinary skill in this art would recognize that certain modifications would come within the scope of this invention. For that reason, the following claims should be studied to determine the true scope and content of this invention.

The invention claimed is:

1. A method of inspecting a component, comprising:
   (a) securing an inspection probe body relative to a component;
   (b) using a sensor assembly housed within the inspection probe body to induce an eddy current in a target area of the component, the target area having a target surface that is spaced from the sensor assembly;
   (c) sensing a parameter of the eddy current in the component using the sensor assembly;
   (d) determining a position of the target surface of the component relative to the inspection probe body using the parameter of eddy current sensed in said step (c); and
   (e) contacting a portion of the component with the inspection probe body during the securing.

2. The method of claim 1, wherein a voltage of the eddy current sensed in said step (c) is the parameter of the eddy current used in said step (d).

3. A method of inspecting a component, comprising:
   (a) securing an inspection probe body relative to a component;
   (b) using a sensor assembly housed within the inspection probe body to induce an eddy current in a target area of the component, the target area having a target surface that is spaced from the sensor assembly;
   (c) sensing a parameter of the eddy current in the component using the sensor assembly; and
   (d) determining a position of the target surface of the component relative to the inspection probe body using the parameter of eddy current sensed in said step (c), wherein said step (d) comprises determining a position of the first surface of the component relative to a reference surface of the component.

4. The method of claim 3, including using a second sensor assembly housed within the inspection probe body to induce an eddy current in a second area of the component, the second area having a second surface and the second sensor assembly spaced from the second surface, and determining spacing between the first surface, the reference surface, the second surface, or some combination of these.

5. The method of claim 3, wherein the first surface and the reference surface establish portions of a blade slot in a turbine engine disk.

6. The method of claim 3, wherein the first surface is transverse the reference surface.

7. The method of claim 1, including actuating portions of the inspection probe body to secure the inspection probe body relative to the component.

8. The method of claim 1, wherein the component is a disk in a turbine engine.

9. The method of claim 8, wherein the target surface establishes a portion of an axially extending slot within the disk.

10. The method of claim 1, further comprising moving the inspection probe body into contact with the component during the securing using an actuator.

11. The method of claim 1, wherein the sensor assembly is entirely spaced from the target surface.

12. The method of claim 1, further comprising contacting the portion of the component with the inspection probe body at a position that is directly adjacent the sensor assembly.

13. The method of claim 1, wherein the inspection probe body contacts the portion of the component at one or more reference surfaces and further comprising calculating at least one distance between the one or more reference surfaces and the target surface.

14. The method of claim 1, wherein the sensor assembly is a first sensor assembly and the target surface is a first target surface, and including at least one second sensor assembly housed within the inspection probe body, the at least one second sensor assembly associated with at least one respective second target surface of the component, and further comprising calculating the position of the at least one second target surface relative to the first target surface.

15. A method of inspecting a component, comprising:
   (a) moving an inspection probe body into contact with a portion of turbine machinery component;
   (b) using a sensor assembly housed within the inspection probe body to induce an eddy current in a target area of the turbine machinery component, the target area having a target surface that is spaced from the sensor assembly;
   (c) sensing a parameter of the eddy current in the turbine machinery component using the sensor assembly; and
   (d) determining a position of the target surface of the component relative to the inspection probe using the parameter of eddy current sensed in said step (c).

* * * * *